United States Patent [19]

Woodle

[11] 4,124,896
[45] Nov. 7, 1978

[54] MISCIBILITY TEMPERATURE SIGNAL MEANS

[75] Inventor: Robert A. Woodle, Nederland, Tex.

[73] Assignee: Texaco Inc., New York, N.Y.

[21] Appl. No.: 730,488

[22] Filed: Oct. 7, 1976

[51] Int. Cl.² ............... G01N 25/00; C10G 21/00
[52] U.S. Cl. .................. 364/557; 196/14.52;
203/2; 364/497; 422/68; 422/119
[58] Field of Search .......... 235/151.3, 151.34, 151.35,
235/151.12; 137/90; 222/54; 23/267 MS, 267
B, 230 A, 230 R; 203/1, 2; 364/557, 496, 497,
502, 500; 208/33, 311, DIG. 1, 314, 327;
196/14.52, 46

[56] References Cited
U.S. PATENT DOCUMENTS

| 3,660,644 | 5/1972 | Hammond et al. | 235/151.34 |
| 3,818,200 | 6/1974 | Pilhofer | 235/151.3 |
| 3,905,229 | 9/1975 | Togo et al. | 235/151.34 |
| 3,972,779 | 8/1976 | Harrison | 235/151.12 |

Primary Examiner—Malcolm A. Morrison
Assistant Examiner—Errol A. Krass
Attorney, Agent, or Firm—Thomas H. Whaley; Carl G. Ries; Ronald G. Gillespie

[57] ABSTRACT

Apparatus provides a signal corresponding to a miscibility temperature for a solvent-oil mixture in a solvent refining unit. The apparatus includes a circuit receiving signals related to flow rates of solvent and charge oil for the solvent refining unit. The circuit provides a signal corresponding to the solvent dosage. A network provides the miscibility temperature signal in accordance with the solvent dosage signal from the circuit.

6 Claims, 1 Drawing Figure

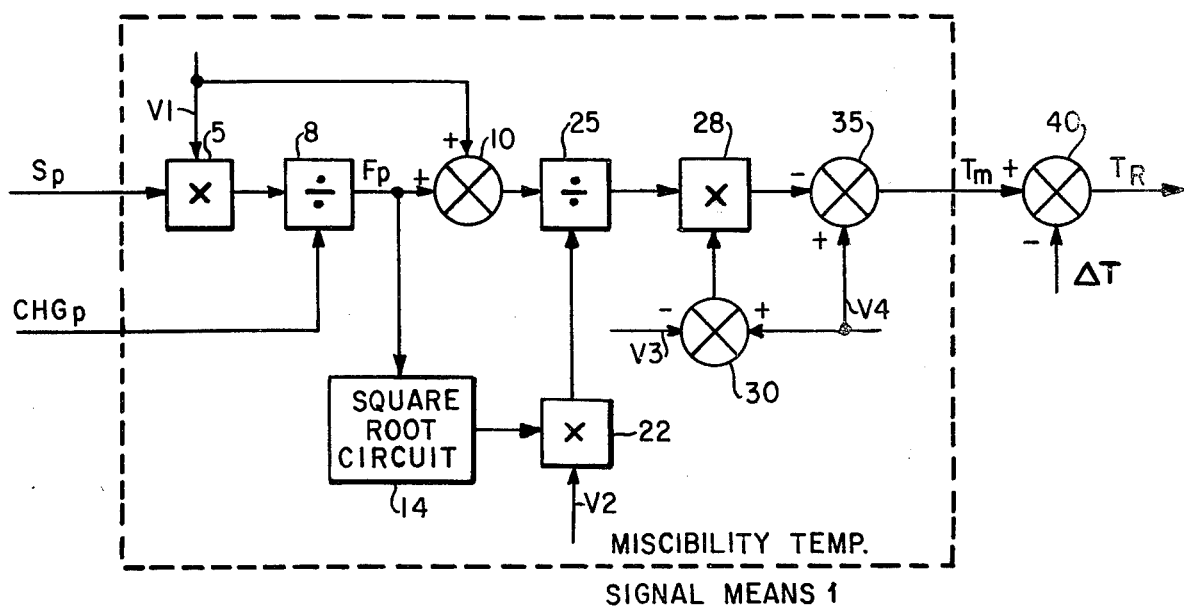

MISCIBILITY TEMPERATURE SIGNAL MEANS

BACKGROUND OF THE INVENTION

Field of the Invention

The present invention relates to signal-producing apparatus in general and, more particularly, to apparatus producing a temperature signal.

SUMMARY OF THE INVENTION

Apparatus provides a signal corresponding to the miscibility temperature of a mixture of oil and solvent for a solvent refining unit. The apparatus includes a circuit adapted to receive signals, representative of flow rates of solvent and charge oil for the solvent refining unit, and provides a signal corresponding to the solvent dosage in accordance with received signals. A network provides the miscibility signal in accordance with the solvent dosage signal from the circuit.

The objects and advantages of the invention will appear more fully hereinafter from a consideration of the detailed description which follows, taken together with the accompanying drawing wherein one embodiment of the invention is illustrated by way of example. It is to be expressly understood, however, that the drawing is for illustration purposes only and is not to be construed as defining the limits of the invention.

DESCRIPTION OF THE DRAWING

The drawing is a simplified block diagram of apparatus, constructed in accordance with the present invention, for providing a signal corresponding to a miscibility temperature for a mixture of oil and solvent.

DESCRIPTION OF THE INVENTION

Referring to the FIGURE, signals $S_P$ and $CHG_P$, corresponding to a sensed solvent flow rate and a sensed charge oil flow rate in a furfural solvent refining unit (not shown) are received by a miscibility temperature signal means 1. Signal means 1 includes a multiplier 5 which multiplies signal $S_P$ with a direct current voltage $V_1$, corresponding to a value of 100, to provide a signal which is divided with signal $CHG_P$ by a divider 8, to provide a signal $F_P$, corresponding to the furfural dosage. The furfural dosage, along with the furfural point $T_{FP}$, is used to determine the miscibility temperature $T_M$ in °F using the following equation:

$$T_M = 323 - [(F+100)(323 - T_{FP})/(20F^{0.5})]$$

$T_{FP}$ is the furfural point temperature in °F and, for a particular charge oil, $T_{FP}$ is determined by laboratory analysis.

Signal $F_P$ is summed with voltage $V_1$, by summing 10, to provide a signal corresponding to the term $(F+100)$ in the equation.

Signal $F_P$ is also provided to a conventional type square root circuit 14 which provides a signal corresponding to the term $F^{0.5}$ in the equation. A multiplier 22 multiplies the signal from circuit 14 with a direct current voltage $V_2$, corresponding to the term 20 in the equation. A divider 25 divides the signal from summing means 10 with the signal from multiplier 22 to provide a signal to a multiplier 28.

Subtracting means 30 subtracts a direct current voltage $V_3$, corresponding to the furfural point temperature $T_{FP}$, from another direct current voltage $V_4$, corresponding to the term 323. Multiplier 28 multiplies the signals from divider 25 and subtracting means 30 to provide a signal to subtracting means 35. Subtracting means 35 subtracts the signal from multiplier 28 from voltage $V_4$ to provide the miscibility temperature signal $T_m$.

Signal $T_M$ may be used as a monitoring signal. Signal $T_M$ may have a predetermined temperature signal $\Delta T$ subtracted from it by subtracting means 40 to provide a reference signal $T_R$. Such a reference signal may be utilized in a control system such as described and disclosed in U.S. Pat. No. 4,053,744 issued on Oct. 11, 1977 and assigned to Texaco Inc., assignee of the present application.

The apparatus of the present invention as hereinbefore described provides a signal corresponding to the miscibility temperature in accordance with the charge oil flow rate and the solvent flow rate.

What is claimed is:

1. Apparatus for providing a signal corresponding to the miscibility temperature of a mixture of solvent and oil for a solvent refining unit, comprising means receiving signals S and CHG corresponding to flow rates of solvent and charge oil, respectively, for providing a signal F, corresponding to the solvent dosage, in accordance with signals S and CHG; and means connected to the F signal means for providing a signal $T_M$, corresponding to a miscibility temperature of a mixture of solvent and oil in accordance with signal F.

2. Apparatus as described in claim 1 in which the solvent is furfural and the $T_M$ signal means provides the $T_M$ signal in accordance with the following equation:

$$T_M = 323 - [(F+100)(323 - T_{FP})/(20F_{0.5})]$$

where $F$ is furfural dosage and $T_{FP}$ is furfural point temperature.

3. Apparatus as described in claim 2 in which the F signal means receives a direct current voltage $V_1$ corresponding to a value of 100 and includes first multiplier means connected to the receiving means for multiplying voltage V1 with signal S to provide a first product signal, and first dividing means connected to the receiving means and to the first multiplying means for dividing the first product signal with signal CHG to provide the signal F.

4. Apparatus as described in claim 3 in which the $T_M$ signal means receives direct current voltages $V_1$, $V_2$, $V_3$ and $V_4$, corresponding to a value of 100, to a value of 20, to the furfural point temperature $T_{FP}$ and to a value of 323, respectively; and includes summing means connected to the first divider means for summing signal F with voltage $V_1$ to provide a sum signal, square root means connected to the first dividing means for providing a signal corresponding to $F^{0.5}$ in accordance with signal F; second multiplier means connected to the square root means for multiplying the signal from the square root means with voltage $V_2$ to provide a second product signal; a second divider means connected to the summing means and to the second multiplier means for dividing the sum signal with the second product signal; first subtracting means for subtracting for voltage $V_3$ from voltage $V_4$ to provide a difference signal; third multiplier means connected to the second divider means and to the first subtracting means for multiplying the signal from the second divider means with the difference signal to provide a third product signal; and second subtracting means connected to the third multiplier means for subtracting the third product signal from voltage $V_4$ to provide signal $T_M$.

5. Apparatus as described in claim 1 further comprises third subtracting means receiving a direct current voltage $\Delta T$ corresponding to a predetermined temperature change and being connected to the second subtracting means for subtracting voltage $\Delta T$ from signal $T_M$ to provide a reference temperature signal $T_R$ which is substantially less than the miscibility temperature.

6. Apparatus as described in claim 5 in which the solvent is furfural and the $T_M$ signal means provides the signal $T_M$ in accordance with the following equation:

$$T_M = 323 - [(F+100)(323-T_{FP})/(20F^{0.5})]$$

where $F$ is the furfural dosage and $T_{FP}$ is the furfural point temperature.

* * * * *